United States Patent
Eckert et al.

(10) Patent No.: US 6,927,302 B2
(45) Date of Patent: Aug. 9, 2005

(54) PROCESS FOR THE ARYLATION OF OLEFINS

(75) Inventors: Markus Eckert, Köln (DE); Albert Schnatterer, Leverkusen (DE); Walter Lange, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 345 days.

(21) Appl. No.: 10/217,222

(22) Filed: Aug. 12, 2002

(65) Prior Publication Data

US 2003/0050500 A1 Mar. 13, 2003

(30) Foreign Application Priority Data

Aug. 13, 2001 (DE) .......................... 101 39 722

(51) Int. Cl.$^7$ .............................. C07C 69/76
(52) U.S. Cl. ...................... 560/104; 502/495
(58) Field of Search .................. 560/104; 562/495

(56) References Cited

U.S. PATENT DOCUMENTS

| | | | |
|---|---|---|---|
| 5,231,223 A | 7/1993 | Bader et al. | 562/87 |
| 5,274,171 A | 12/1993 | Chalk et al. | 560/104 |
| 5,300,675 A | 4/1994 | Elango | 560/55 |
| 5,360,924 A | 11/1994 | Beller et al. | 560/55 |

OTHER PUBLICATIONS

Palladium Reagents in Organic Synthesis, Academic Press, (month unavailable) 1985, R.F. Heck, pp. 287–290 "Mixed Coupling Reactions of Aryl and Alkenyl Derivatives".

Kikukawa et al.: "Palladium(0)–Catalyzed Arylation of Olefin by Arylamines and Alkyl Nitrite" J. Org. Chem., Bd. 46, 1981, Seiten 4885–4888, XP000882385 Tabelle II; Tabelle III; Tablelle IV, Seiten 4886, "Equation 1".

Org. Chem., Bd. 46, 1981, Seiten 4885–4888, XP000882385 Tabelle II; Tabelle III; Tablelle IV, Seiten 4886, "Equation 1".

*Primary Examiner*—Paul J. Killos
(74) *Attorney, Agent, or Firm*—Godfried R. Akorli; Diderico van Eyl

(57) ABSTRACT

The present invention encompasses a process for preparing arylolefins by reacting one or more arylamines with one or more organic nitrites, in the presence of one or more olefins which bear at least one hydrogen atom on the double bond and in the presence of acid and in the presence of palladium or one or more palladium compounds.

25 Claims, No Drawings

PROCESS FOR THE ARYLATION OF OLEFINS

BACKGROUND OF THE INVENTION

1. Field of the Invention

The invention relates to a process for the arylation of olefins by reaction of aromatic diazonium salts with olefins in the presence of a palladium catalyst.

2. Brief Description of the Prior Art

Arylolefins play an important role both as active compounds or intermediates for active compounds in light stabilizers and pharmaceuticals and also in the preparation of dyes. The palladium-catalysed reaction of diazonium salts with olefins is known, for example, from R. F. Heck, Palladium Reagents in Organic Synthesis, Academic Press, 1985, p. 287–290. EP-A 508 264, too, describes a process which exploits this reaction for the synthesis of arylolefins. However, the disadvantage of this process is the fact that substituted anilines are firstly converted into the corresponding diazonium salts and the reaction with olefins is only carried out subsequently with the addition of palladium compounds. On an industrial scale, this procedure has the disadvantage that large amounts of diazonium salts are present in the intervening period and these pose a considerable safety risk and also, owing to their sparing solubility, frequently result in process engineering problems.

The process of EP-A 606 057, which requires isolated diazonium salts as starting material, also has the abovementioned disadvantages.

EP-A 553 668 describes a process for preparing arylacrylic acid derivatives in which substituted anilines are firstly diazotized and the diazonium salts are subsequently, without intermediate isolation, reacted further to form arylacrylic acid derivatives by use of carboxylic acids as solvent. However, this process does not prevent an accumulation of diazonium salts either.

There was therefore a need to develop a process which, starting from substituted or unsubstituted aminoaryl compounds, allows the palladium-catalysed preparation of arylolefins, with the diazonium salt formed as an intermediate being reacted further in situ.

SUMMARY OF THE INVENTION

In accordance with the foregoing, the present invention encompasses a process for preparing arylolefins which is characterized in that one or more arylamines are reacted with one or more organic nitrites in the presence of one or more olefins which bear at least one hydrogen atom on the double bond and in the presence of acid and in the presence of palladium or one or more palladium compounds or palladium and one or more palladium compounds.

DETAILED DESCRIPTION OF THE INVENTION

The process of the invention is preferably carried out using one arylamine, one olefin and palladium or one palladium compound and also one organic nitrite.

As arylamines, one can use, for example, carbocyclic aromatic or heteroaromatic amines.

In the present context, arylamines are, for example, compounds of the formula (I)

$$Ar-(NH_2)_n \qquad (I)$$

where n is one or two and

Ar may be a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the molecule, can be replaced by heteroatoms selected from the group consisting of nitrogen, sulphur and oxygen. Furthermore, the carbocyclic aromatic radicals or heteroaromatic radicals may be substituted by up to five identical or different substituents per ring which are selected from the group consisting of OH, iodine, bromine, chlorine, fluorine, nitro, cyano, free or protected formyl, $C_1$–$C_{12}$-alkyl, $C_6$–$C_{12}$-aryl, $C_7$–$C_{13}$-arylalkyl, $C_1$–$C_8$-hydroxyalkyl, $C_1$–$C_8$-hydroxyalkoxy, $C_1$–$C_8$-hydroxyalkylamino, —PO—[($C_1$–$C_8$)-alkyl]$_2$, —PO—[($C_6$–$C_{12}$)-aryl]$_2$, tri($C_1$–$C_6$-alkyl)siloxyl and radicals of the formula (II), $$A-B-D-E \qquad (II)$$

where, independently of one another,

A is absent or is a $C_1$–$C_8$-alkylene radical and

B is absent or is oxygen, sulphur or $NR^1$, where $R^1$ is hydrogen, $C_1$–$C_8$-alkyl, $C_7$–$C_{10}$-arylalkyl or $C_6$–$C_{10}$-aryl and D is a carbonyl group and E is $R^2$, $OR^2$, $NHR^3$ or $N(R^3)_2$, where $R^2$ is $C_1$–$C_8$-alkyl, $C_7$–$C_{10}$-arylalkyl, $C_1$–$C_8$-hydroxyalkyl, $C_1$–$C_8$-haloalkyl or $C_6$–$C_{10}$-aryl and $R^3$ are each, independently of one another, $C_1$–$C_8$-alkyl, $C_1$–$C_8$-hydroxyalkyl, $C_7$–$C_{10}$-arylalkyl or $C_6$–$C_{10}$-aryl or $N(R^3)_2$ together forms a cyclic amino radical, and radicals of the formulae (IIIa–e)

| | |
|---|---|
| A—E | (IIIa) |
| A—SO$_2$-E | (IIIb) |
| A—B—SO$_2$R$^2$ | (IIIc) |
| A—SO$_3$X | (IIId) |
| A—COX | (IIIe) | where A, B, E and $R^2$ are as defined above and X is OH, $NH_2$, or OM, where M can be an alkali metal ion, half an equivalent of an alkaline earth metal ion, an ammonium ion or an organic ammonium ion.

In all cases in which arylamines of the formula (I) are substituted by carboxylic or sulphonic acid groups, they can also be present as an internal salt.

In the abovementioned contexts, alkyl or alkylene is in each case independently a straight-chain, cyclic, branched or unbranched alkyl or alkylene radical. The same applies to the alkyl part of an arylalkyl radical.

The general term aryl includes not only carbocyclic radicals but also encompasses heteroaromatic radicals in which no, one, two or three framework carbon atoms per ring, but at least one framework carbon atom in the total radical, is/are replaced by heteroatoms selected from the group consisting of nitrogen, sulphur and oxygen.

The same applies to the aryl part of an arylalkyl radical.

In the above-mentioned contexts, haloalkyl is in each case independently a straight-chain, cyclic, branched or unbranched alkyl radical which may be monosubstituted, polysubstituted or persubstituted by halogen atoms selected independently from the group consisting of fluorine, chlorine and bromine.

In the above-mentioned contexts, hydroxyalkyl is in each case independently a straight-chain, cyclic, branched or unbranched alkyl radical which may be substituted by one or more hydroxy groups in such a way that each carbon atom bears the radical of not more than one oxygen, sulphur or nitrogen atom.

The term protected formyl refers to a formyl radical which is protected by conversion into an aminal, acetal or a mixed aminal-acetal, with the aminals, acetals and mixed aminal-acetals being able to be acyclic or cyclic.

There are no restrictions in respect of the radiochemical arrangement of the above-mentioned substituents relative to the amino group or the amino groups.

Examples of carbocyclic aromatic radicals having from 6 to 18 framework carbon atoms are phenyl, naphthyl, phenanthrenyl, anthracenyl or fluorenyl. Examples of heteroaromatic radicals having from 5 to 18 framework carbon atoms in which no, one, two or three framework carbon atoms per ring, but at least one framework carbon atom in the total molecule, can be replaced by heteroatoms selected from the group consisting of nitrogen, sulphur and oxygen are pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, triazolyl or quinolinyl.

Examples of compounds of the formula (I) are the isomeric aminobenzenesulphonic acids, e.g. 2-, 3- and 4-aminobenzenesulphonic acids, the isomeric diaminobenzenesulphonic acids, e.g. 2,4-diaminobenzenesulphonic acid or 2,5-diaminobenzenesulphonic acid, the isomeric aminobenzenedisulphonic acids, e.g. aminobenzene-2,4-disulphonic acid, aminobenzene-3,5-disulphonic acid and aminobenzene-2,5-disulphonic acid, the isomeric diaminobenzenedisulphonic acids, e.g. 1,4-diaminobenzene-2,6-disulphonic acid or 1,3-diaminobenzene-4,6-disulphonic acid, also 2-, 3- or 4-aminobenzoic acid, $C_1$–$C_{12}$-alkyl esters of 2-, 3- or 4-aminobenzoic acid, e.g. methyl 2-, 3- or 4-aminobenzoate, ethyl 2-, 3- or 4-aminobenzoate, n-propyl 2-, 3- or 4-aminobenzoate, i-propyl 2-, 3- or 4-aminobenzoate, n-butyl 2-, 3- or 4-aminobenzoate, $C_6$–$C_{16}$-aryl esters of 2-, 3- or 4-aminobenzoic acid, e.g. phenyl 2-, 3- or 4-aminobenzoate, 3- or 4-aminobenzene-1,2-dicarboxylic acid, di-$C_1$–$C_{12}$-alkyl esters of 3- or 4-aminobenzene-1,2-dicarboxylic acid, e.g. dimethyl 3- or 4-aminobenzene-1,2-dicarboxylate or diethyl 3- or 4-aminobenzene-1,2-dicarboxylate, 3- or 4-aminobenzene-1,2-dicarboxylic anhydride, 2-, 3- or 4-aminobenzonitrile, 3- or 4-aminophthalonitrile or amino-$C_1$–$C_{12}$-alkoxybenzenes. e.g. 2-, 3- or 4-aminomethoxybenzene, 2-, 3- or 4-aminoethoxybenzene, 2-, 3- or 4-amino-tert-butoxybenzene, 2-, 3- or 4-amino-phenyl $C_6$–$C_{19}$-aryl ethers, 2-, 3- or 4-aminonitrobenzene, 2-, 3- or 4-aminofluorobenzene, 2-3- or 4-aminochlorobenzene, 2-, 3- or 4-aminobromobenzene, 2-, 3- or 4-aminoiodobenzene, the isomeric amino-fluorochlorobenzenes, e.g. 3-amino-2-fluorochlorobenzene, the isomeric aminobromochlorobenzenes, the isomeric aminofluorobromobenzenes, the isomeric aminodifluorobenzenes, the isomeric aminodichlorobenzenes, the isomeric aminodibromobenzenes, the isomeric aminodiiodobenzenes, 2-, 3- or 4-amino(trifluoromethylbenzene), 2-, 3- or 4-aminophenyl $C_1$–$C_{12}$-alkyl ketones, e.g. 2-, 3- or 4-amino-acetophenone, 2-, 3- or 4-aminophenyl $C_6$–$C_{10}$-aryl ketones, e.g. 2-, 3- or 4-aminobenzophenone, 2-, 3- or 4-amino-$C_1$–$C_{12}$-alkylbenzenes, e.g. 2-, 3- or 4-aminotoluene, the isomeric 2-, 3- or 4-aminodi-$C_1$–$C_{12}$-alkylbenzenes, e.g. 3- or 4-amino-o-xylene, the isomeric diamino-$C_1$–$C_{12}$-alkylbenzenes, e.g. 2,3-diaminotoluene, 2,4-diaminotoluene, 2,5-diaminotoluene or 2,6-diaminotoluene, also diaminodi-$C_1$–$C_{12}$-alkylbenzenes, 2-, 3- or 4-amino-$C_6$–$C_{10}$arylbenzenes, e.g. 2-, 3- or 4-aminobiphenyl, 2-, 3- or 4-aminoaminobenzene, 2-, 3- or 4-aminophenol. Mention may also be made of the isomeric aminonaphthalenesulphonic acids, e.g. 8-amino-2-naphthalenesulphonic acid, 8-amino-1-naphthalenesulphonic acid, 7-amino-1-naphthalenesulphonic acid, 6-amino-2-napthalenesulphonic acid, 5-amino-2-naphthalenesulphonic acid, 5-amino-1-naphthalenesulphonic acid, 4-amino-2-naphthalenesulphonic acid, 2-amino-naphthalene-1-sulphonic acid, 1-amino-2-naphthalenesulphonic acid, the isomeric aminonaphthalenedisulphonic acids, e.g. 7-amino-1,3-naphthalenedisulphonic acid, 3-amino-2,6-naphthalenedisulphonic acid, 3-amino-2,7-naphthalenedisulphonic acid, 4-amino-1,3-naphthalenedisulphonic acid, 4-amino-1,5-naphthalenedisulphonic acid, 4-amino-1,6-naphthalenedisulphonic acid, 4-amino-1,7-naphthalenedisulphonic acid, 4-amino-2,6-naphthalenedisulphonic acid, 6-amino-1,3-naphthalenedisulphonic acid, 8-amino-1,3-naphthalenedisulphonic acid, 3-amino-1,5-naphthalenedisulphonic acid, 4-amino-2,7-naphthalenedisulphonic acid, 5-amino-1,3-naphthalenedisulphonic acid, the isomeric diamino-naphthalenesulphonic acids and diaminonaphthalenedisulphonic acids, e.g. 3,4-bis(amino)-1-naphthalenesulphonic acid, 4,5-diamino-1-naphthalenesulphonic acid, 3,8-diamino-1,5-naphthalenedisulphonic acid, 4,8-diamino-2,6-naphthalenedisulphonic acid, 5,6-diamino-1,3-naphthalenedisulphonic acid, 4,5-diamino-2,7-naphthalenedisulphonic acid, also diaminobiphenylmonosulphonic and diaminobiphenyldisulphonic acids, e.g. 4,4'-diaminobiphenyl-3-sulphonic acid and 4,4'-diaminobiphenyl-3,3'-disulphonic acid.

Further examples which may be mentioned are 2-, 3-, 4-aminopyridine and 2-, 3-, 4-, 5-, 6-, 7-, 8-aminoquinoline.

Preferred compounds of the formula (I) are those in which n is one and Ar is phenyl, naphthyl, anthracenyl, phenanthrenyl, pyridinyl, pyrazinyl, pyridazinyl or pyrimidinyl which is substituted by no, one, two or three further substituents per ring which are selected from the group consisting of OH, bromine, chlorine, fluorine, cyano, methyl, ethyl, n-propyl, isopropyl, n-butyl, n-pentyl, n-hexyl, phenyl, benzyl, trifluoromethyl, pentafluoroethyl, trichloromethyl, —PO—[($C_1$–$C_8$)-alkyl]$_2$, —PO—[($C_6$–$C_{12}$)-aryl]$_2$ and substituents of the formulae (II) and (IIIa-e) in which, in each case independently of one another, A is absent or is methylene or 1,2-ethylene, B is absent or is oxygen or $NR^1$, where $R^1$ is hydrogen. methyl, ethyl or propyl and D is a carbonyl group and E is $R^2$, $OR^2$, $NHR_3$ or $N(R^3)_2$, where $R^2$ is methyl, ethyl, n-propyl, isopropyl, n-butyl, tert-butyl, benzyl, 2-hydroxyethyl, trifluoromethyl or phenyl and $R^3$ are each, independently of one another, methyl, ethyl, n-propyl, isopropyl, n-butyl, benzyl, 2-hydroxyethyl or phenyl or $N(R^3)_2$ together is morpholinyl, piperidinyl or pyrrolidinyl and X is OH, $NH_2$, or OM, where M is a sodium, potassium or ammonium ion.

Particularly preferred compounds are those of the formula (I) in which n is one and Ar is phenyl which is substituted by no, one or two further substituents selected from the group consisting of fluorine, cyano, methyl, ethyl, phenyl, trifluoromethyl and radicals of the formulae (II) and (IIIa, d,e) in which A and B are absent and D is a carbonyl group and E is $R^2$, $OR^2$, $NHR^3$ or $N(R^3)_2$, where $R^2$ is methyl, ethyl or phenyl and $R^3$ are each, independently of one another, methyl, ethyl or phenyl and X is OH, $NH_2$ or ONa.

Very particular preference is given to 4-methoxyaminobenzene.

As olefins which bear at least one hydrogen atom on the double bond, it is possible to use, for example, those of the formula (V),

$$R^5CH=CR^6R^7 \quad (V)$$

where, independently of one another, $R^5$ is hydrogen or methyl and $R^6$ is hydrogen or methyl and $R^7$ can be hydrogen, cyano, $SO_3M$, $C_1$–$C_8$-alkyl, a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the total molecule, can be replaced by heteroatoms selected from the group consisting of nitrogen, sulphur and oxygen or is a radical of the formula (VI)

(VI)

where G is OM, OH, $NH_2$, $OR^8$, $NHR^8$ or $N(R^8)_2$ and $R^8$ is $C_1$–$C_{12}$-alkyl, $C_7$–$C_{12}$-arylalkyl or $C_6$–$C_{10}$-aryl or $N(R^8)_2$ together is a cyclic amino radical and M can be an alkali metal ion, half an equivalent of an alkaline earth metal ion, an ammonium ion or an organic ammonium ion.

Furthermore, the carbocyclic aromatic radicals or heteroaromatic radicals may, for example, be substituted by up to three identical or different substituents per ring which are selected from the group consisting of iodine, bromine, chlorine, fluorine, nitro, cyano, free or protected formyl, $C_1$–$C_{12}$-alkyl, $C_6$–$C_{12}$-aryl, $C_7$–$C_{13}$-arylalkyl, $C_1$–$C_8$-alkoxy, $C_1$–$C_8$-alkoxycarbonyl, $C_1$–$C_8$-haloalkoxy, $NH(C_1$–$C_8$-alkyl), $N(C_1$–$C_8$-alkyl)$_2$.

Examples of olefins of the formula (V) are ethene, propene, butene, 1,1,1-trifluoro-2-propene, substituted or unsubstituted vinyl-$C_6$–$C_{10}$-aromatics, e.g. styrene or the isomeric vinylnaphthalenes, 2-, 3- or 4-fluorostyrene, 2-, 3- or 4-chlorostyrene, 2-, 3- or 4-bromostyrene, 2-, 3- or 4-iodostyrene, 2-, 3- or 4-cyanostyrene, 2-, 3- or 4-($C_1$–$C_{12}$)-alkoxystyrene such as 2-, 3- or 4-methoxystyrene, 2-, 3- or 4-nitrostyrene, 2-, 3- or 4-styrenecarboxylic acid, $C_1$–$C_{12}$-alkyl 2-, 3- or 4-styrenecarboxylates such as methyl 2-, 3- or 4-styrenecarboxylate, $C_6$–$C_{12}$-aryl 2-, 3- or 4-styrenecarboxylates such as phenyl 2-, 3- or 4-styrenecarboxylate, 2-, 3- and 4-styrenesulphonic acids and their salts, 3- or 4-vinylphthalic acid, di-$C_1$–$C_{12}$-alkyl 3- or 4-vinylphthalates such as dimethyl 3- or 4-vinylphthalate, di-$C_6$–$C_{10}$-aryl 3- or 4-vinylphthalates such as diphenyl 3- or 4-vinylphthalate, 3- or 4-vinylphthalic anhydride, vinylhetaryls such as N-vinylimidazole or 2- or 4-vinylpyridine, also acrylonitrile, acrylic acid, $C_1$–$C_{12}$-alkyl acrylates such as methyl acrylate, ethyl acrylate, n-propyl acrylate, 2-ethylhexyl acrylate, vinylsulphonic acid and the salts thereof.

Very particularly preferred olefins having at least one hydrogen substituent are ethylene, propene, acrylonitrile, acrylic acid, methyl acrylate, 2-ethylhexyl acrylate and 1,1,1-trifluoro-2-propene.

The amount of olefin used can be, for example, from 0.5 to 200 times the molar amount of the amino groups of the arylamine which are to be reacted, preferably from 0.9 to 5 times this molar amount and very particularly preferably from 1.0 to 1.2 times this molar amount.

Suitable acids are, for example, sulphuric acid, hydrohalic acids such as hydrogen chloride, hydrogen bromide or hydrogen iodide, phosphoric acid, acetic acid, propionic acid, methanesulphonic acid, trifluoromethane-sulphonic acid, tetrafluoroboric acid or hexafluorophosphoric acid or mixtures thereof. The acids can also be used in the form of aqueous solutions.

Preference is given to using concentrated sulphuric acid, aqueous solutions of hydrochloric acid or acetic acid or mixtures thereof; very particular preference is given to concentrated sulphuric acid.

The amount of acid used can be, for example, from 0.1 to 10 times the molar amount of the amino groups to be diazotized, preferably from 0.5 to 2 times this molar amount.

If free acid groups are present in the arylamine used or the olefin used, the amount of acid can be reduced correspondingly.

Palladium can be used in the process of the invention in the form of, for example, palladium black or palladium applied to support materials, for example palladium on activated carbon.

Suitable palladium compounds are, for example, palladium-phosphine complexes which are either prepared in situ from palladium salts and phosphine ligands or are used as isolated palladium-phosphine complexes.

As isolated palladium-phosphine complexes, it is possible to use, for example, those of the formula (VIIa),

$$[PdL_2An_2] \quad (VIIa)$$

where

L are each a monophosphine or $L_2$ together are a diphosphine and

An is the anion of an acid, or those of the formula (VIIb)

$$[PdL_4] \quad (VIIb)$$

where L can each be a monophosphine or half an equivalent of a diphosphine.

Monophosphines can, for example, be ones of the formula (VIII)

$$P(R^9)_3 \quad (VIII)$$

where the radicals $R^9$ are each, independently of one another, straight-chain, branched or cyclic $C_1$–$C_8$-alkyl or phenyl or naphthyl which may be unsubstituted or substituted by one, two or three radicals $R^{10}$, where $R^{10}$ is straight-chain, branched or cyclic $C_1$–$C_8$-alkyl, straight-chain, branched or cyclic $C_1$–$C_8$-alkoxy, chlorine, fluorine, $N(C_1$–$C_6$-alkyl$)_2$, $CO_2$—$(C_1$–$C_6$-alkyl), —$CON(C_1$–$C_6$-alkyl$)_2$, cyano or $C_1$–$C_6$-acyl.

Preferred monophosphines are triphenylphosphine and tris-o-tolylphosphine.

Diphosphines can be, for example, ones of the formula (IX), $$(R^{11})_2P\text{—}A\text{—}P(R^{11})_2 \quad (IX)$$

where the radicals $R^{11}$ are each, independently of one another, straight-chain or cyclic, branched or unbranched $C_1$–$C_8$-alkyl or phenyl, naphthyl or heteroaryl having from 5 to 12 framework carbon atoms which may be unsubstituted or substituted by one, two or three radicals $R^{12}$, where $R^{12}$ are selected independently from the group consisting of straight-chain, branched or cyclic $C_1$–$C_8$-alkyl, straight-chain, branched or cyclic $C_1$–$C_6$-alkoxy, fluorine and cyano and A is an unsubstituted or substituted radical selected from the group consisting of $C_1$–$C_4$-alkylene, 1,2-phenyl, 1,2-cyclohexyl, 1,1'-ferrocenyl, 1,2-ferrocenyl, 2,2'-(1,1'-binaphthyl) and 1,1'-biphenyl.

Preferred diphosphines are bis(diphenylphosphino) ethane, 1,3-bis-(diphenylphosphino)propane and 1,4-bis (diphenylphosphino)butane.

The anion of an acid can, for example, be selected from the group consisting of chloride, bromide, iodide, acetate and nitrate.

Further palladium compounds which can be used are, for example, $Pd_2$(dibenzylideneacetone)$_3$ or allylpalladium chloride or bromide or compounds of the formula (Xa), $$Pd(Y^1)_2 \quad (Xa)$$

where $Y^1$ is chloride, bromide, acetate, nitrate, methanesulphonate, trifluoromethanesulphonate or acetylacetonate, or palladium compounds of the formula (Xb)

$$Pd(Y^2)_2L_2 \quad (Xb)$$

where $Y^2$ is chloride, bromide, acetate, methanesulphonate, trifluoromethanesulphonate, tetrafluoroborate or hexafluorophosphate and L are each acetonitrile, benzonitrile or benzyl nitrile, or $L_2$ together is 1,5-cyclooctadiene, or palladium compounds of the formula (Xc)

$$M_2[Pd(Y^3)_4] \quad (Xc),$$

where $Y^3$ is chloride or bromide and

M is lithium, sodium, potassium, ammonium or organic ammonium.

Preference is given to palladium on carbon and palladium, palladium acetate, palladium chloride, palladium bromide, lithium, sodium and potassium tetrachloropalladate and tetrabromopalladate, and also PdCl$_2$(triphenylphosphine)$_2$, PdBr$_2$(triphenylphosphine)$_2$, PdI$_2$(triphenylphosphine)$_2$, PdCl$_2$(tris-o-tolylphosphine)$_2$, PdBr$_2$(tris-o-tolylphosphine)$_2$, PdI$_2$(tris-o-tolylphosphine)$_2$, PdCl$_2$(bis (diphenylphosphino)ethane), PdBr$_2$(bis(diphenylphosphino) ethane), PdI$_2$(bis(diphenylphosphino)ethane), PdCl$_2$(1,3-bis (diphenylphosphino)propane), PdBr$_2$(1,3-bis (diphenylphosphino)propane), PdI$_2$(1,3-bis (diphenylphosphino)propane), PdCl$_2$(1,4-is (diphenylphosphino)butane), PdBr$_2$(1,4-bis (diphenylphosphino)butane), PdI$_2$(1,4-bis (diphenylphosphino)butane) and also palladium complexes which are generated in situ from any combinations of palladium acetate, palladium nitrate, palladium chloride, palladium bromide, lithium, sodium and potassium tetrachloropalladate and tetrabromopalladate and triphenylphosphine, tri-o-tolylphosphine, bis (diphenylphosphino)ethane, 1,3-bis(diphenylphosphino) propane or 1,4-bis(diphenylphosphino)butane. Further palladium compounds which may be mentioned are Pd$_2$ (dibenzylideneacetone)$_3$ and Pd(triphenylphosphine)$_4$.

Very particular preference is given to palladium on carbon, palladium acetate and Pd$_2$ (dibenzylideneacetone)$_3$.

The amount of palladium used or palladium compounds used can be, for example, from 0.0001 to 10 mol % based on the aryl compound used; preference is given to from 0.001 to 5 mol % and very particular preference is given to from 0.01 to 2 mol %.

As organic nitrites, one can use, for example, those of the formula (IV), $$R^4ONO \quad (IV)$$

where $R^4$ is, for example, straight-chain or branched, cyclic or acyclic $C_1$–$C_8$-alkyl or $C_7$–$C_9$-arylalkyl, or mixtures of such nitrites.

Preference is given to using in each case only one nitrite of the formula (IV) in which R is benzyl, methyl, ethyl, n-propyl, isopropyl, n-butyl, isobutyl, tert-butyl, n-pentyl, isopentyl, neopentyl, n-hexyl or 2-ethylhexyl.

Organic nitrites which are very particularly preferred in the process of the invention are methyl nitrite and tert-butyl nitrite.

The organic nitrites are either commercially available or can be prepared in a manner known per se by a person skilled in the art, for example by reacting the parent alcohol with nitrite salts such as sodium nitrite in the presence of acid.

The amount of organic nitrite used can, for example, be from 0.8 to 5 times the molar amount of the amino groups to be diazotized, preferably from 0.9 to 1.5 times this molar amount and very particularly preferably from 1.0 to 1.3 times this molar amount.

The reaction temperature can be, for example, from 0 to 150° C., preferably from 10 to 100° C. and very particularly preferably from 50 to 90° C.

If desired, one or more organic solvents can also be added to the reaction mixture.

Examples of Suitable Organic Solvents are:

Alcohols such as methanol, ethanol, n-propanol, isopropanol, n-butanol, isobutanol, tert-butanol, n-pentanol, isopentanol, neopentanol, n-hexanol, cyclohexanol and 2-ethylhexanol, or polar aprotic solvents such as N-methylpyrrolidone, dimethyl sulphoxide, tetramethylene sulphone, dimethylformamide, N-methylcaprolactam, acetonitrile or benzonitrile.

If the olefin used for the reaction is liquid over at least part of the temperature range indicated, it can itself be used as solvent.

The pressure is generally not critical and can be, for example, from 0.5 to 20 bar. Preference is given to ambient pressure. This also makes it possible for the liquefied olifin to be used as solvent. The reaction is preferably carried out with very substantial exclusion of oxygen.

Furthermore, compounds which serve as free-radical scavengers and/or reducing agents can be added to the reaction. Examples of such compounds are hydroquinone, hydroquinone monomethyl ether, 2,6-di-tert-butylphenol, 2,6-di-tert-butyl-4-methylphenol and 2-tert-butyl-5-methylphenol.

It is possible, for example, to place the arylamine, the olefin, the organic nitrite and the palladium catalyst in a reaction vessel and to start the reaction by addition of acid.

In a preferred embodiment of the process of the invention, the procedure is, for example, to place the olefin, the arylamine, the acid, the palladium catalyst and any solvent in a reaction vessel and to add the organic nitrite at the desired reaction temperature. After addition of the organic nitrite is complete, the mixture can, if appropriate, be stirred for a further period at the same temperature.

In a further preferred embodiment of the process of the invention, specific arylolefins, namely cinnamic acid derivatives, are prepared by reacting one or more arylamines with one or more organic nitrites in the presence of one or more olefins of the formula (V) in which $R^5$ and $R^6$ can have the widest abovementioned meaning and $R^7$ can be a radical of the formula (VI),

(VI)

where G is OM, OH, $OR^8$, where $R^8$ can be $C_1$–$C_{12}$-alkyl, $C_7$–$C_{12}$-arylalkyl or $C_6$–$C_{10}$-aryl and M can be an alkali metal ion, half an equivalent of an alkaline earth metal ion, an ammonium ion or an organic ammonium ion, in the presence of acid and in the presence of palladium or one or more palladium compounds or palladium and one or more palladium compounds, in the presence of an alcohol of the formula (XI)

$$R^{13}OH \qquad (XI)$$

where $R^{13}$ is $C_1$–$C_{12}$-alkyl or $C_7$–$C_{13}$-arylalkyl and in the presence or absence of one or more solvents.

Preference is given in each case to using one arylamine, one olefin and one organic nitrite.

In this case, the amount of alcohol of the formula (XI) used can be from 0.5 to 200 times the molar amount of amino groups of the arylamine to be reacted, preferably from 0.8 to 50 times this molar amount and particularly preferably from 1.0 to 10 times this molar amount.

In a further variant for preparing substituted cinnamic acids, the organic nitrite used can advantageously be derived from the alcohol of the formula (XI) which is used.

The arylolefins prepared according to the invention are particularly useful, for example, for preparing pharmaceuticals or their intermediates and for preparing compounds for protection against light, in particular UV-A and UV-B light filters, or their intermediates.

Furthermore, the arylolefins prepared according to the invention are suitable for preparing dye preparations or their intermediates.

The particular advantage of the process of the invention is the fact that the catalytic reaction of the diazonium salt produced as an intermediate commences immediately on formation of the diazonium salt and prior isolation of the diazonium salts which pose safety problems in handling or their accumulation in the reaction medium can therefore be prevented. A further advantage of the process of the invention is that in the preparation of substituted cinnamic esters, both the esterification and the arylation of the acrylic acid derivative used can be carried out in a single-vessel reaction.

The invention is further illustrated but is not intended to be limited by the following examples in which all parts and percentages are by weight unless otherwise specified.

EXAMPLES

Example 1

6.2 g of 4-methoxyaminobenzene (p-anisidine) were dissolved in 75 ml of 2-ethylhexanol (isooctanol) and admixed with 2 ml of concentrated sulphuric acid. Under a nitrogen atmosphere, 0.12 g of palladium acetate, 0.07 g of hydroquinone, 1.3 g of triphenylphosphine and 9.4 g of 2-ethylhexyl acrylate were added and the mixture was heated to 80° C. while stirring. At this temperature, methyl nitrite which had been formed by introducing 12 ml of 48% strength sulphuric acid into a solution of 7 g of sodium nitrite in 4 g of methanol and 21 ml of water was passed into the suspension over a period of one hour. The mixture was then stirred for another one hour. The mixture was filtered with suction while hot and the crude solution was distilled under reduced pressure. This gave 8.6 g of isooctyl 4-methoxycinnamate (60% of theory).

Example 2

6.2 g of 4-methoxyaminobenzene (p-anisidine) were dissolved in 40 ml of NMP and admixed with 2 ml of concentrated sulphuric acid. Under a nitrogen atmosphere, 0.6 g of palladium on activated carbon (palladium content= 5%), 0.07 g of hydroquinone and 9.4 g of 2-ethylhexyl acrylate were added and the mixture was heated to 80° C. while stirring. At this temperature, 7 ml of t-butyl nitrite were added dropwise to the suspension over a period of one hour. The mixture was then stirred for another one hour. The mixture was filtered with suction while hot and the crude solution was distilled under reduced pressure. This gave 11.7 g of isooctyl 4-methoxycinnamate (81% of theory).

Example 3

6.2 g of 4-methoxyaminobenzene (p-anisidine) were dissolved in 40 ml of 2-ethylhexanol (isooctanol) and admixed with 2 ml of concentrated sulphuric acid. Under a nitrogen atmosphere, 0.6 g of palladium on activated carbon (palladium content=5%), 0.07 g of hydroquinone and 4.2 ml of acrylic acid were added and the mixture was heated to 75° C. while stirring. At this temperature, 7 ml of t-butyl nitrite were added dropwise to the suspension over a period of one hour. The mixture was then stirred for another one hour. The mixture was filtered with suction while hot and the crude solution was distilled under reduced pressure. This gave 7.5 g of isooctyl 4-methoxycinnamate (52% of theory).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing arylolefins by palladium-catalysed coupling of aryldiazonium salts and olefins, comprising reacting:
   one or more arylamines
   with one or more organic nitrites,
   in the presence of one or more olefins which bear at least one hydrogen atom on the double bond and
   in the presence of acid and
   in the presence of palladium or one or more palladium compounds.

2. Process according to claim 1, wherein the arylamine is reacted with one organic nitrite in the presence of an olefin which bears at least one hydrogen atom on the double bond and in the presence of palladium or one palladium compound.

3. Process according to claim 1 wherein one or more organic solvents are added.

4. Process according to claim 1 wherein the reaction is carried out in the presence of one or more free-radical scavengers.

5. Process according to claim 1 wherein the reaction is carried out in the presence of one or more reducing agents.

6. Process according to claim 1 wherein the arylamines used are carbocyclic aromatic or heteroaromatic amines.

7. Process according to claim 1 wherein the arylamines used have the formula (I)

$$\text{Ar—(NH}_2)_n \qquad \text{(I)}$$

where
n is one or two and
Ar is a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the molecule, is replaced by heteroatoms selected from the group consisting of nitrogen, sulphur and oxygen and the carbocyclic aromatic radicals or heteroaromatic radicals are furthermore substituted by up to five identical or different substituents per ring which are selected from the group consisting of OH, iodine, bromine, chlorine, fluorine, nitro, cyano, free or protected formyl, $C_1$–$C_{12}$-alkyl, $C_6$–$C_{12}$-aryl, $C_7$–$C_{13}$-arylalkyl, $C_1$–$C_8$-hydroxyalkyl, $C_1$–$C_8$-hydroxyalkoxy, $C_1$–$C_8$-hydroxyalkylamino, —PO—[($C_1$–$C_8$)-alkyl]$_2$, —PO—[($C_6$–$C_{12}$)-aryl]$_2$, tri($C_1$–$C_6$-alkyl)siloxyl and radicals of the formula (II), $$\text{A—B—D—E} \qquad \text{(II)}$$

where, independently of one another,
A is absent or is a $C_1$–$C_8$-alkylene radical and
B is absent or is oxygen, sulphur or $NR^1$,
where $R^1$ is hydrogen, $C_1$–$C_8$-alkyl, $C_7$–$C_{10}$-arylalkyl or $C_6$–$C_{10}$-aryl and
D is a carbonyl group and
E is $R^2$, $OR^2$, $NHR^3$ or $N(R^3)_2$,
where $R^2$ is $C_1$–$C_8$-alkyl, $C_7$–$C_{10}$-arylalkyl, $C_1$–$C_8$-hydroxyalkyl, $C_1$–$C_8$-haloalkyl or $C_6$–$C_{10}$-aryl and
$R^3$ are each, independently of one another, $C_1$–$C_8$-alkyl, $C_1$–$C_8$-hydroxyalkyl, $C_7$–$C_{10}$-arylalkyl or $C_6$–$C_{10}$-aryl or
$N(R^3)_2$ together forms a cyclic amino radical,
and radicals of the formulae (IIIa–e)

| | |
|---|---|
| A—E | (IIIa) |
| A—SO$_2$—E | (IIIb) |
| A—B—SO$_2$R$^2$ | (IIIc) |
| A—SO$_3$X | (IIId) |
| A—COX | (IIIe) | where A, B, E and $R^2$ are as defined above and X is OH, $NH_2$, or OM, where M is an alkali metal ion, half an equivalent of an alkaline earth metal ion, an ammonium ion or an organic ammonium ion.

8. Process according to claim 1 wherein the olefins bearing at least one hydrogen atom on the double bond which are used have the formula (V), $$R^5CH=CR^6R^7 \qquad \text{(V)}$$

where, independently of one another,
$R^5$ is hydrogen or methyl and
$R^6$ is hydrogen or methyl and
$R^7$ is hydrogen, cyano, $SO_3M$, $C_1$–$C_8$-alkyl, a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the total molecule, is replaced by heteroatoms selected from the group consisting of nitrogen, sulphur and oxygen
or is a radical of the formula (VI)

where G is OM, OH, $NH_2$, $OR^8$, $NHR^8$ or $N(R^8)_2$ and $R^8$ is $C_1$–$C_{12}$-alkyl, $C_7$–$C_{12}$-arylalkyl or $C_6$–$C_{10}$-aryl or $N(R^8)_2$ together is a cyclic amino radical and M is an alkali metal ion, half an equivalent of an alkaline earth metal ion, an ammonium ion or an organic ammonium ion and
the carbocyclic aromatic radicals or heteroaromatic radicals are further substituted by up to three identical or different substituents per ring which are selected from the group consisting of iodine, bromine, chlorine, fluorine, nitro, cyano, free or protected formyl, $C_1$–$C_{12}$-alkyl, $C_6$–$C_{12}$-aryl, $C_7$–$C_{13}$-arylalkyl, $C_1$–$C_8$-alkoxy, $C_1$–$C_8$-alkoxycarbonyl, $C_1$–$C_8$-haloalkoxy, $NH(C_1$–$C_8$-alkyl), $N(C_1$–$C_8$-alkyl)$_2$.

9. Process according to claim 1 wherein the acid used is sulphuric acid, hydrochloric acid or acetic acid.

10. Process according to claim 1 wherein the organic nitrites used have the formula (IV), $$R^4ONO \qquad \text{(IV)}$$

where
R$^4$ is, straight-chain or branched, cyclic or acyclic C$_1$–C$_8$-alkyl or C$_7$–C$_9$-arylalkyl, or mixtures of the organic nitrites.

11. Process according to claim 1 wherein the amount of palladium used or the palladium compound used is from 0.0001 to 10 mol % based on the aryl compound used.

12. Process according to claim 1 wherein the reaction is conducted at a temperature from 0 to 150° C.

13. Process for preparing cinnamic acid derivatives by palladium-catalysed coupling of aryldiazonium salts and olefins, comprising reacting:
  one or more arylamines
  with one or more organic nitrites
  in the presence of one or more olefins of the formula (V), $$R^5CH=CR^6R^7 \quad (V)$$

where
R$^5$ is hydrogen or methyl and
R$^6$ is hydrogen or methyl and
R$^7$ is a radical of the formula (VI),

(VI)

where G is OM, OH, OR$^8$, where R$^8$ can be C$_1$–C$_{12}$-alkyl, C$_7$–C$_{12}$-arylalkyl or C$_6$–C$_{10}$-aryl and M is an alkali metal ion, half an equivalent of an alkaline earth metal ion, an ammonium ion or an organic ammonium ion,
  in the presence of acid and
  in the presence of palladium or one or more palladium compounds and
  in the presence of an alcohol of the formula (XI)

$$R^{13}OH \quad (XI)$$

where R$^{13}$ is C$_1$–C$_{12}$-alkyl or C$_7$–C$_{13}$-arylalkyl.

14. Process according to claim 13, wherein in each case one arylamine, one olefin and one organic nitrite are used.

15. Process according to claim 13 wherein 4-methoxyaminobenzene is used as arylamine.

16. Process according to claim 13 wherein 2-ethylhexanol is used as alcohol.

17. Process according to claim 13 wherein acrylic acid is used as olefin.

18. Process according to claim 13 wherein one or more organic solvents are added.

19. Process according to claim 13 wherein concentrated sulphuric acid is used as acid.

20. A process for preparing pharmaceuticals or their intermediates comprising providing the arylolefin of claim 1.

21. A process for preparing light stabilizers or their intermediates comprising providing the arylolefins of claim 1.

22. A process for preparing dyes or their intermediates comprising providing the arylolefin of claim 1.

23. A process for preparing pharmaceuticals or their intermediates comprising providing the arylolefin of claim 13.

24. A process for preparing light stabilizers or their intermediates comprising providing the arylolefins of claim 13.

25. A process for preparing dyes or their intermediates comprising providing the arylolefin of claim 13.

* * * * *